US012053251B2

(12) United States Patent
Bono et al.

(10) Patent No.: US 12,053,251 B2
(45) Date of Patent: *Aug. 6, 2024

(54) ROBOTIC SURGICAL CONTROL SYSTEM

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US); Thomas J. Lord, South Milwaukee, WI (US)

(73) Assignee: Globus Medical, Inc., Audubon, PA (US)

( * ) Notice: Subject to any disclaimer, the term of this patent is extended or adjusted under 35 U.S.C. 154(b) by 324 days.

This patent is subject to a terminal disclaimer.

(21) Appl. No.: 17/526,287

(22) Filed: Nov. 15, 2021

(65) Prior Publication Data
US 2022/0071717 A1    Mar. 10, 2022

Related U.S. Application Data

(63) Continuation of application No. 16/245,830, filed on Jan. 11, 2019, now Pat. No. 11,173,000.
(Continued)

(51) Int. Cl.
A61B 34/30    (2016.01)
A61B 17/16    (2006.01)
A61B 17/70    (2006.01)
A61B 34/00    (2016.01)
A61B 34/20    (2016.01)
(Continued)

(52) U.S. Cl.
CPC .......... *A61B 34/30* (2016.02); *A61B 17/1671* (2013.01); *A61B 17/7076* (2013.01); *A61B 17/7082* (2013.01); *A61B 34/20* (2016.02); *A61B 34/25* (2016.02); *A61B 34/37* (2016.02); *A61B 34/74* (2016.02); *A61B 17/1757* (2013.01); *A61B 2034/102* (2016.02); *A61B 2034/107* (2016.02); *A61B 2034/2074* (2016.02); *A61B 34/76* (2016.02); *A61B 2090/031* (2016.02); *A61B 2090/064* (2016.02);
(Continued)

(58) Field of Classification Search
CPC ......... A61B 34/30; A61B 34/37; A61B 34/00; A61B 34/20; A61B 34/74; A61B 34/76; A61B 34/7076; A61B 17/70; A61B 17/16; A61B 17/17; A61B 17/1757; A61B 17/1671

See application file for complete search history.

(56) References Cited

U.S. PATENT DOCUMENTS 6,522,906 B1 *   2/2003   Salisbury, Jr. ....... A61B 1/0005
                                                              600/407
9,820,818 B2 *  11/2017   Malackowski ........ A61B 34/20
(Continued)

FOREIGN PATENT DOCUMENTS

WO    2013192598 A1    12/2013

Primary Examiner — Christopher J Beccia

(57) ABSTRACT

The invention involves a system and method for controlling the movements of a multi-axis robot to perform a surgery at least on the spinal area of a human in vivo. The system includes controls and software coding to cause the robot to move in desired patterns to complete the surgery, which may include bone, disc and tissue removal, and may also include insertion of hardware for fusing adjacent bony structures.

20 Claims, 15 Drawing Sheets

Related U.S. Application Data

(60) Provisional application No. 62/616,700, filed on Jan. 12, 2018.

(51) Int. Cl.
  *A61B 34/37* (2016.01)
  *A61B 17/17* (2006.01)
  *A61B 34/10* (2016.01)
  *A61B 90/00* (2016.01)

(52) U.S. Cl.
  CPC ... *A61B 2090/066* (2016.02); *A61B 2090/364* (2016.02)

(56) References Cited

U.S. PATENT DOCUMENTS

| | | | |
|---|---|---|---|
| 11,173,000 B2* | 11/2021 | Bono | A61B 34/25 |
| 2013/0345718 A1* | 12/2013 | Crawford | A61B 17/8866 606/130 |
| 2015/0100066 A1 | 4/2015 | Kostrzewski et al. | |

* cited by examiner

ROBOTIC SURGICAL CONTROL SYSTEM

PRIORITY CLAIM

The present invention is a continuation of U.S. patent application Ser. No. 16/245,830, filed Jan. 11, 2019, which claims priority to U.S. Provisional Patent Application Ser. No. 62/616,700, entitled "ROBOTIC SURGICAL CONTROL SYSTEM", filed Jan. 12, 2018, all of which are incorporated herein in their entirety.

FIELD OF THE INVENTION

The invention relates to robotic surgical procedures and, more specifically, to a software system configuring a computer system that controls the movements of a multi-axial robot to perform an orthopedic surgical procedure.

BACKGROUND INFORMATION

The performance of an orthopedic surgical procedure on the spine with the assistance of a robot is known in the art. However, the surgeries that have been previously performed are merely small portions of the surgery, or have been small steps in the overall completion of the surgery. Thus, the known control systems configured by software for controlling the movements of the robot are deficient for complex and delicate procedures such as bone removal, disc removal and the like.

Thus, the present invention provides a software configured control system which overcomes the disadvantages of prior art robot surgical systems. The robotic surgical control system of the present invention not only provides for relative ease in the setup of the procedure and control over the robot during the actual 1 operation, it also provides warnings and monitoring of the procedure to detect, warn and prevent injury to a patient undergoing the procedure.

SUMMARY OF THE INVENTION

Briefly, the invention involves a system and method for controlling the movements of a multi-axis robot to perform a surgery at least on the spinal area of a human in vivo. The system includes controls and software coding to cause the robot to move in desired patterns to complete a surgery, which may include bone, disc and tissue removal, and may also include insertion of hardware for fusing adjacent bony structures.

Accordingly, it is an objective of the present invention to provide a system for controlling a multi-axis robot for performance of a surgical procedure.

It is a further objective of the present invention to provide software for controlling the movements of a multi-axis robot for performance of a surgical procedure.

It is yet a further objective of the present invention to provide a method for controlling a multi-axis robot for the purpose of performing a surgical procedure.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

Figure 1:
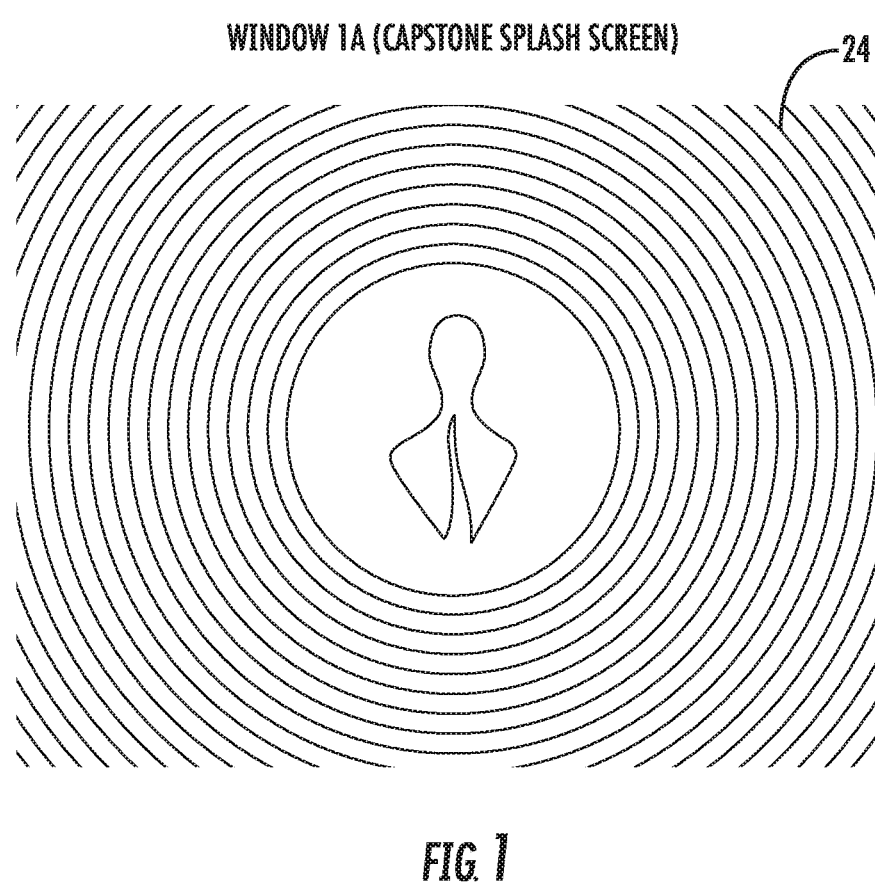
FIG. 1 is a screen shot illustrating the opening screen of the present system.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF PREFERRED EMBODIMENTS

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to FIGS. 1-15, a robotic surgical system 10 that includes a computer system 11 operably connected or interfaced with a multi-axis robot 12 for controlling the movements of components of the multi-axis robot 12 to perform a surgical procedure on a human patient 14 in vivo is illustrated. The computer system 11 includes a user interface 16, shown as two touchscreen displays 18. The primary visual display 20 is positioned above the work display 22, and may be provided with a horizontal tilt toward the operator 68 to facilitate easier tactile interaction. It is contemplated that these touchscreen displays have built-in multi touch support for scrolling, zooming and rotating viewpoints and target objects, in addition to standard click based selection functionality. The displays 20, 22 are operable to display one or more digital images from one or more image files in storage 83. The computer system 11 includes a computer 82 having storage 83 and a processor 84. The computer 82 is operably connected to the robot 12 wirelessly or by suitable wiring 85. The storage 83 can have a primary storage (commonly referred to as memory) and/or a secondary storage device that can be read by the processor 84 to transfer the digital images between the primary storage to the secondary storage for subsequent long-term storage as an image file, such as a jpeg file. Primary and secondary storage are herein referred to as storage collectively, and the term storage can include one or both primary and secondary storage. It is to be understood that the image file can be transferred wirelessly between primary storage and long-term storage. It is also to be understood that long term storage can be remote, for example, cloud storage or other remote storage.

While operational information can be input by a user such as a surgeon via the display 20, 22, it can also be input by other input devices such as a keyboard 87, joystick or mouse 86 and a touchscreen display 18. The information input can be by a user touching the screen on a display 20, 22 with a finger, stylus or other suitable implement. Based upon the commands input into the computer 82, the computer outputs electrical signals to the multi-axis robot 12 to cause the motors in the robot to move the robot's 12 component arms 89 to a desired position at a desired speed. A tool holder 91 is also associated with the robot 12 for holding a suitable surgical tool 92. The motors (not shown) of the robot may be servos or any other type of motor suitable to provide feedback to the computer system 11 and thus the control system 10 to ensure that the movements of the various robotic arms 89 are moving as commanded by the control system. Thus, it is desirable that the robotic motors are provided with, but not limited to, encoders to provide the feedback signals to the control system 10. In this manner, the control system 10 can modify the electrical signals to the robot 12 to provide the desired level of control needed for surgical procedures. In addition, the robot 12 may be provided with torque sensors, G-force sensors, speed sensors, orientation sensors and the like to provide additional feedback data to the control system 10 to further enhance control of the robot's movements.

In at least one embodiment, the multi-axis robot 12 is provided with a mobile base assembly 90. The mobile base assembly 90 allows the control system 10 to reposition the robot 12 for a more desirable position for completing the desired operation based upon fiducial landmarks in the patient's anatomy, which may be marked to provide electrical, magnetic induced or other types of signals that allow the control system to position the robot. These movements may be based upon limitations in the robot's ability to move in a desired trajectory or the like. In at least one embodiment, the base assembly 90 is provided with Mecanum wheels 92, which allow movement of the robot in any direction without rotation of the wheel about a vertical axis. Like the robot axes, the Mecanum wheel should be provided with motors and/or sensors that provide feedback to the control system 10, which has the capability to monitor the movement, and alter the movement, in real time based upon discrepancies such as wheel slippage and the like.

Figure 2:
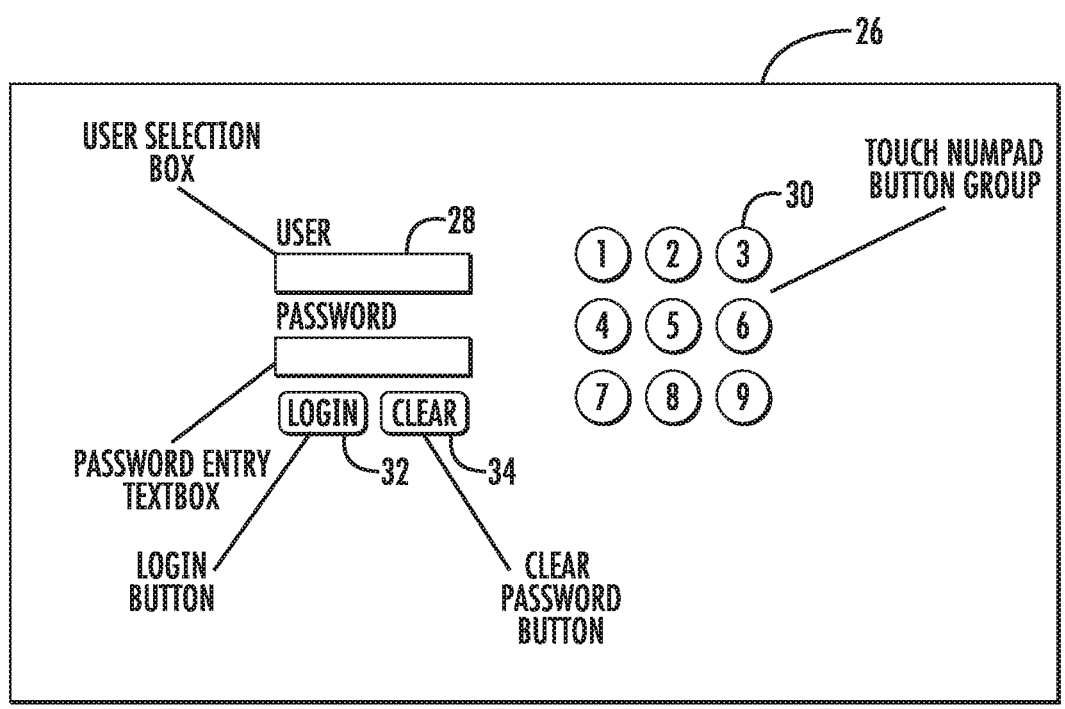
FIG. 2 is a screen shot illustrating a login screen for the present system.

Referring to FIGS. 1 and 2, the startup and login screens are illustrated. The startup screen 24 is initially viewed when the system is started. Once started, the login screen 26 becomes viewable. To login, the user or operator 68 selects their name from a list of registered users and places their name in the user box. Thereafter, the operator 68 enters a numeric or other suitable password to open the system using the keypad 30 or keyboard 87. The data is entered into the computer using the login button 32, or cleared with the clear button 34. It should also be noted that other types of logins may be utilized without departing from the scope of the invention, which may include, but should not be limited to, retina scans, facial scans, fingerprint scans, RFID, and other suitable methods of determining the true identity of an operator 68.

Figure 3:
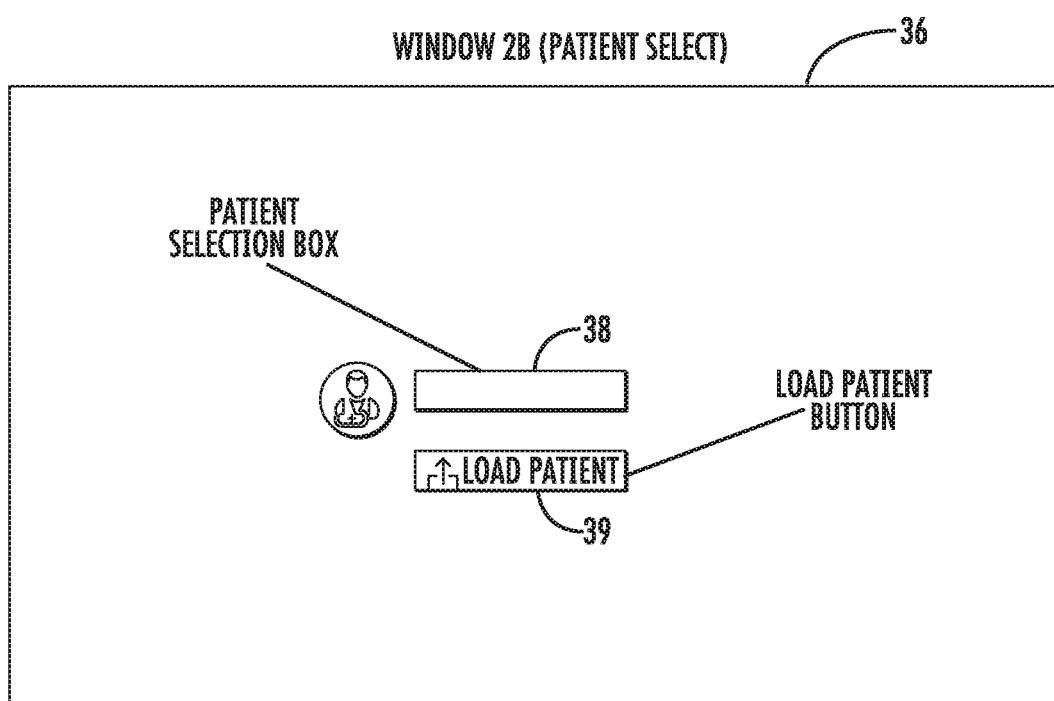
FIG. 3 is a screen shot illustrating a patient selection screen for the present system.

Referring to FIG. 3, the patient selection screen is illustrated. To select a patient, the operator 68 may type in or scroll through a list of preloaded patient profiles. The patient's name is then entered into the patient selection box 38 and the load patient button 39 selects the named patient. Once selected, the patient's imaging and medical data (FIG. 4) are available for the operator 68, and the system progresses to the next screen.

Figure 4:
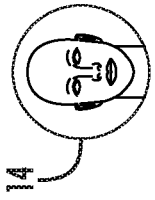
FIG. 4 is a screen shot illustrating a patient information screen for the present system.

Referring to FIG. 4, the patient information screen 40 is illustrated. In this screen, patient details 42 are viewed on the work display 22. Various surgical procedure types 46 are listed in the navigation toolbar 44 for selection by the operator 68.

Figure 5:
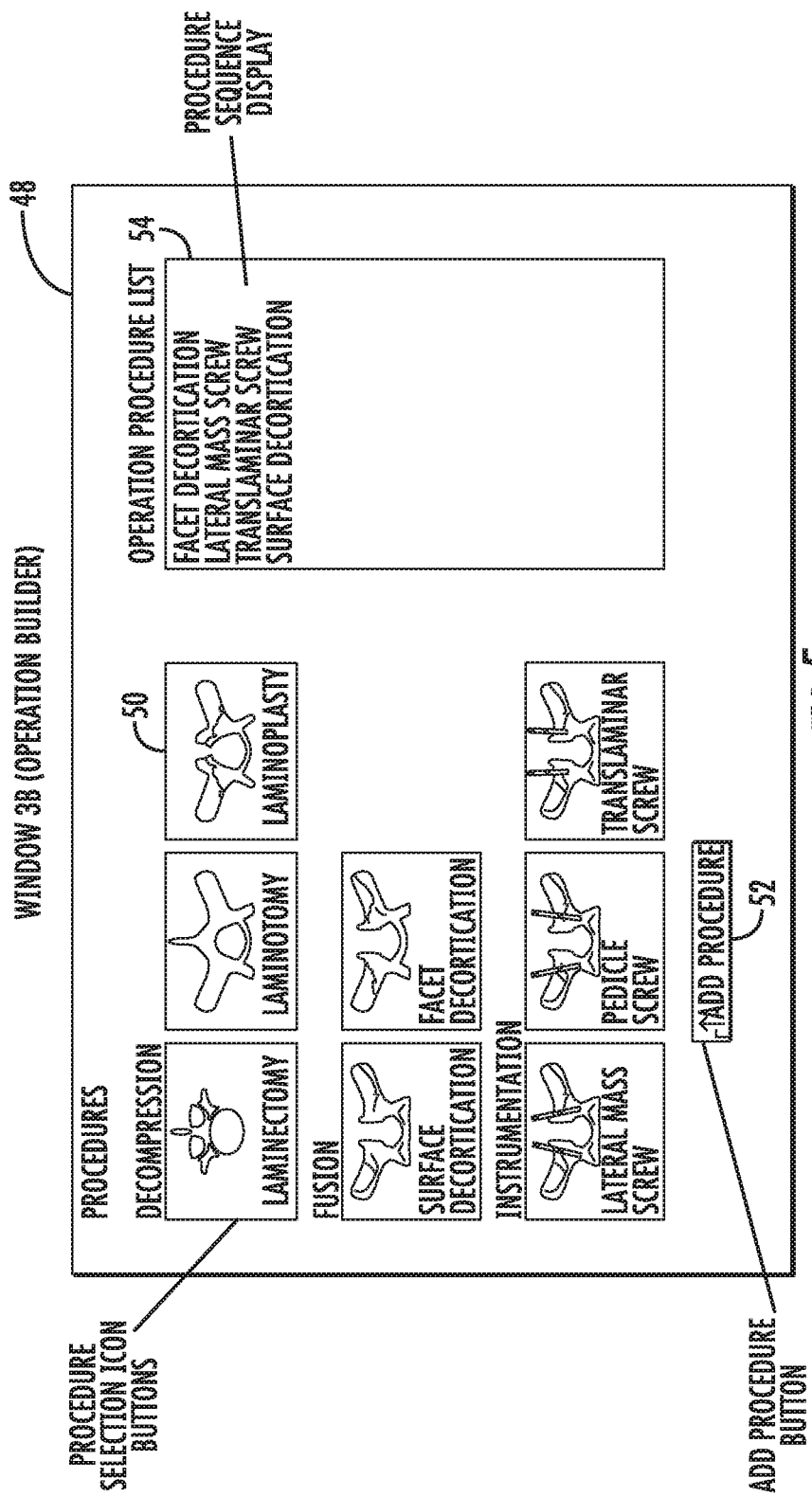
FIG. 5 is a screen shot illustrating a procedure selection screen for the present system.

Referring to FIG. 5, the operation builder screen 48 is illustrated. Each surgical procedure 46 is provided with picture icons 50. Selection of the desired procedure and pressing the add procedure button 52 appends the sequence of operations in the Operation Procedure List 54 with the steps associated to the selected procedure. The selections made on this screen determine available options on planner screens, see FIGS. 6 and 7. Pressing procedure types 46 on the navigation toolbar 44 (FIG. 4) allows the operator 68 to toggle to and from the operation builder screen 48 throughout operation of the system 10.

Figure 6:
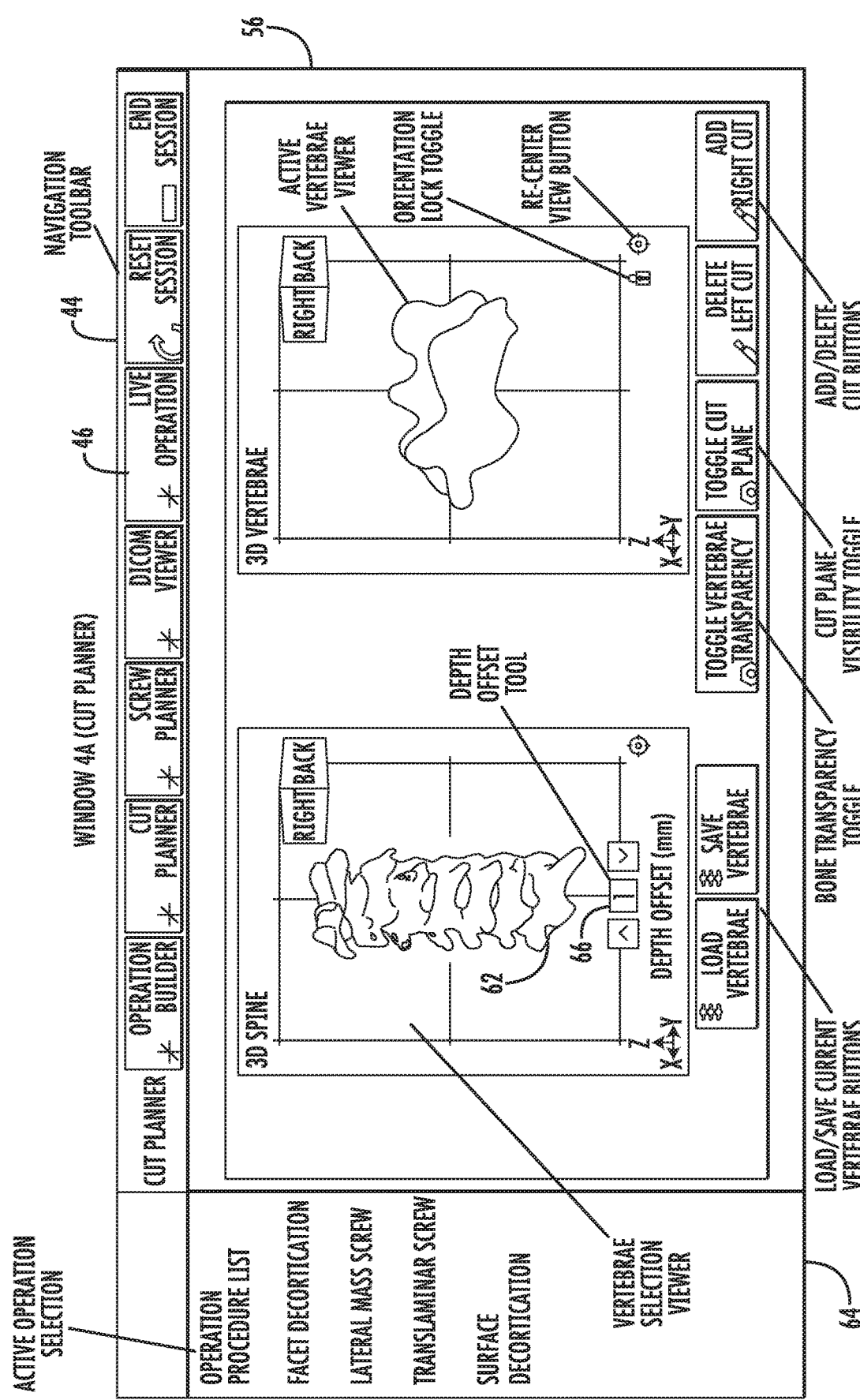
FIG. 6 is a screen shot illustrating a cut planning screen for the present system.
Figure 7:
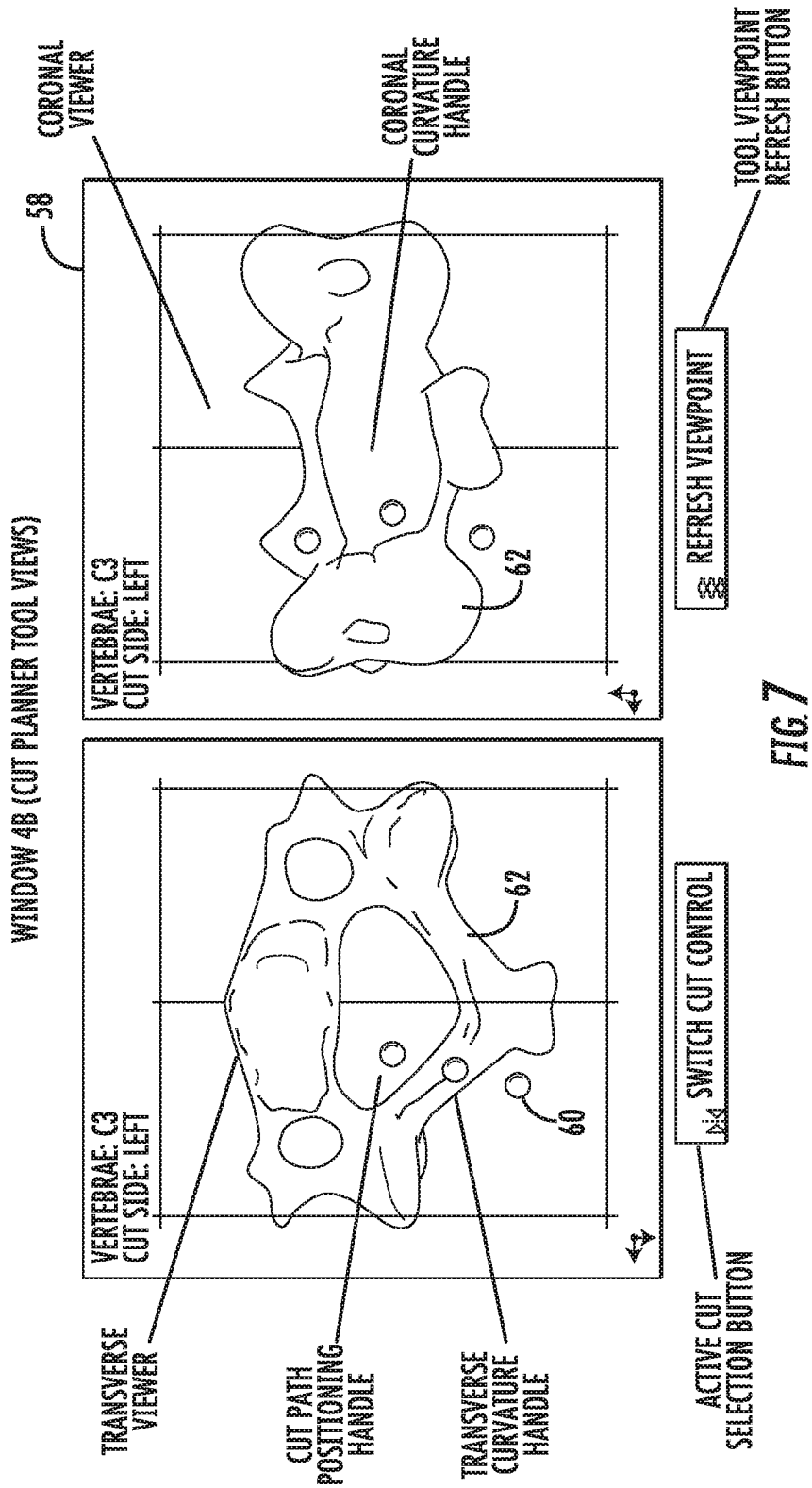
FIG. 7 is a screen shot illustrating a cutting tool path screen for the present system.

Referring to FIGS. 6 and 7, the cut planner screens 56, 58 are illustrated. In these screens 56, 58, the system 10 allows the operator 68 to select vertebrae 62 and edit cutter paths 60 for the procedure. A proposed surgical tool path 60 is input by the operator as described above on a screen on at least one of the displays 20, 22. The specific procedure to be edited is selected from the Operation Procedure List 64 on the left side of the screen. Each procedure can include operations on any number of vertebrae 62. Tool selection buttons 66 allow the user to select the type of tool to be used for cutting. Each tool selected has an associated tool offset length and diameter to automatically offset and establish the cutting depth of the tool relative to the tool path chosen and directed by the operator 68 for the procedure. All tools chosen are stored for tool path generation. The navigation bar 44 allows the operator 68 to toggle into and out of this screen throughout the procedure as desired. In this manner, the operator 68 can change the surgical tool paths and tools used for the procedure as desired. The on screen view of vertebrae 62 can be rotated and enlarged to allow the surgical tool path 60 to be placed as desired by the operator 68. In this manner, the operator 68 can view the surgical tool path 60 from various angles, and can zoom in on specific features that are desired to remain or be cut away.

Figure 8:
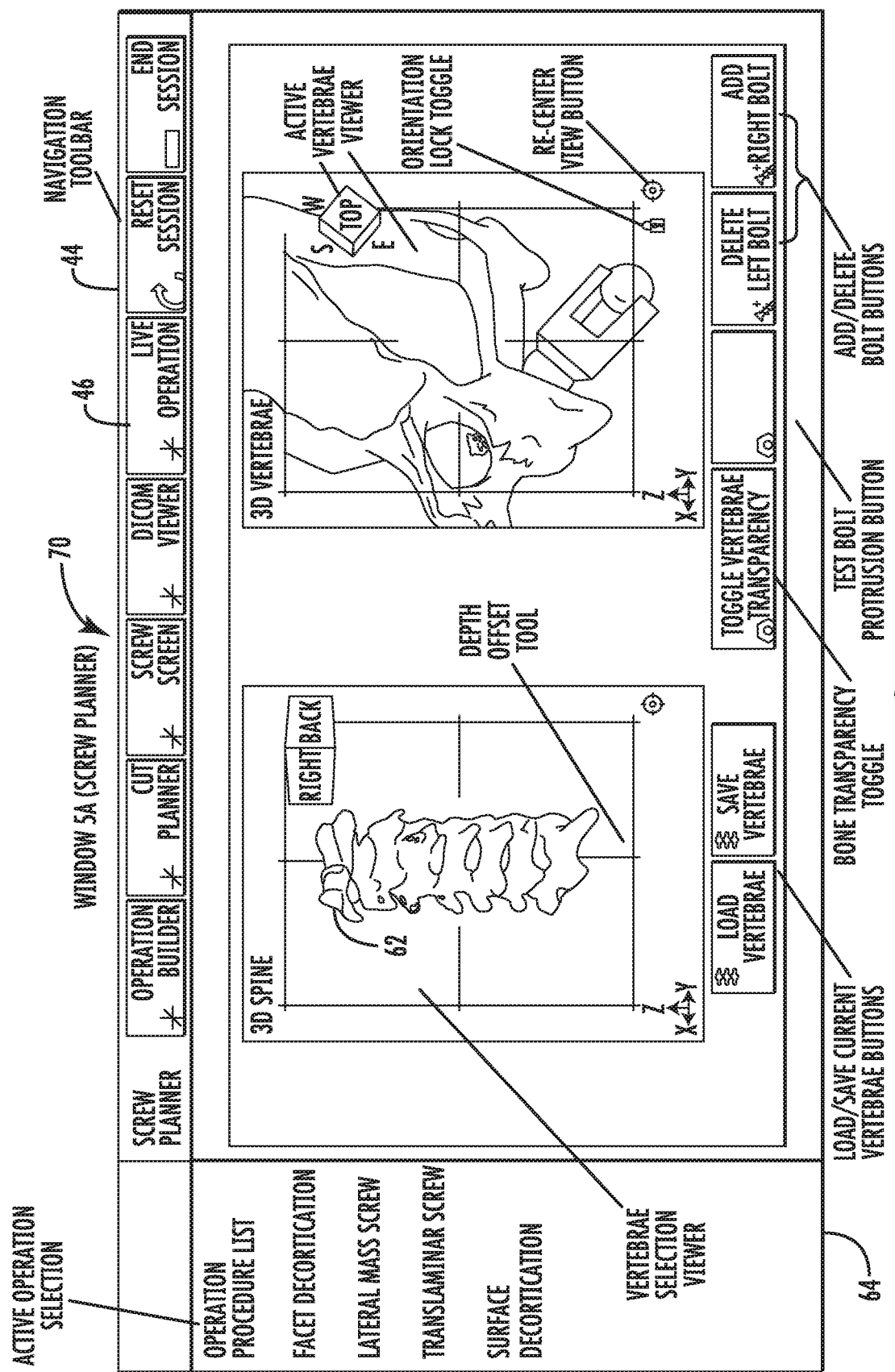
FIG. 8 is a screen shot illustrating a screw insertion planning screen for the present system.
Figure 9:
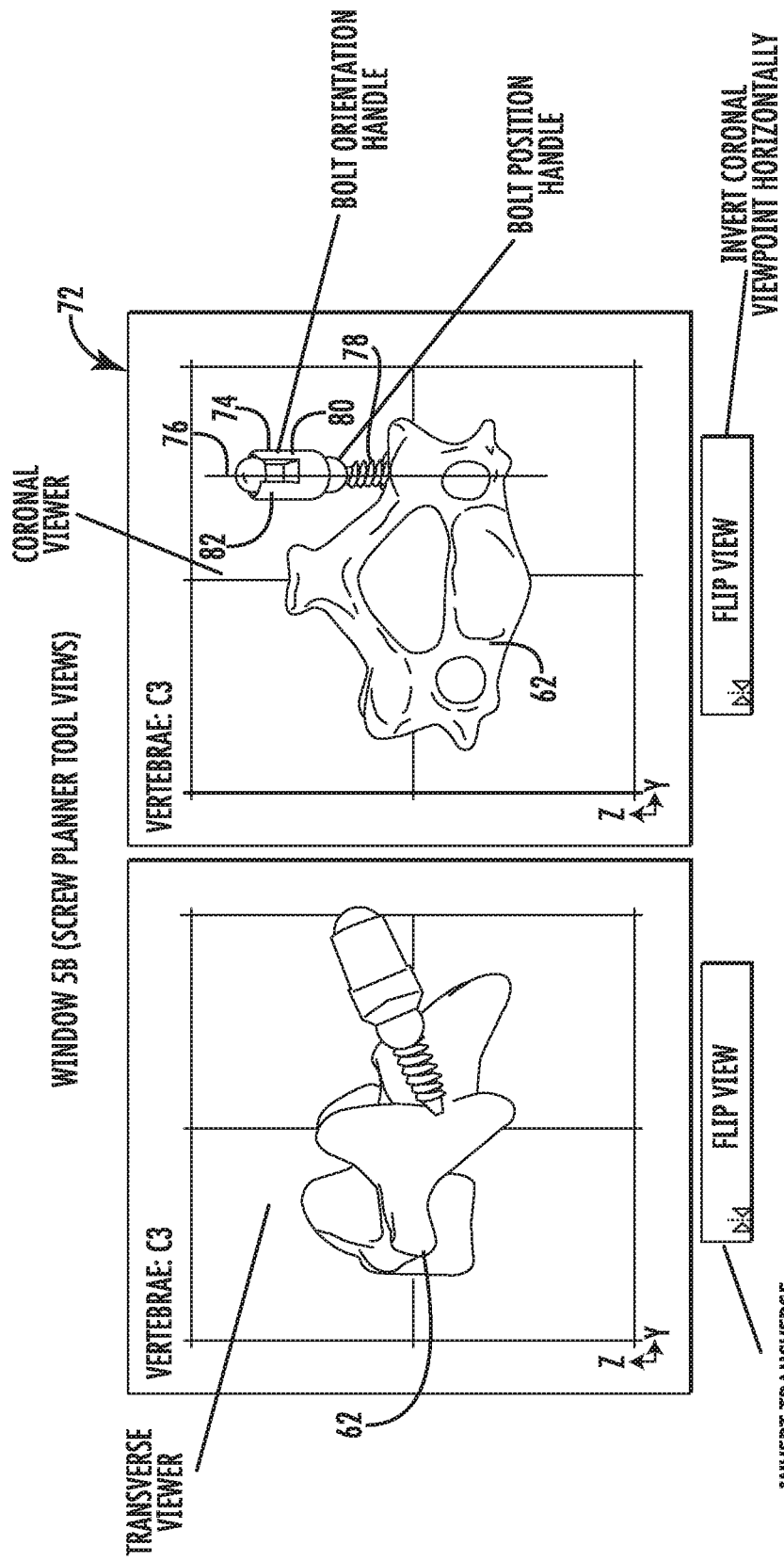
FIG. 9 is a screen shot illustrating another screw insertion planning screen for the present system.
Figure 10:
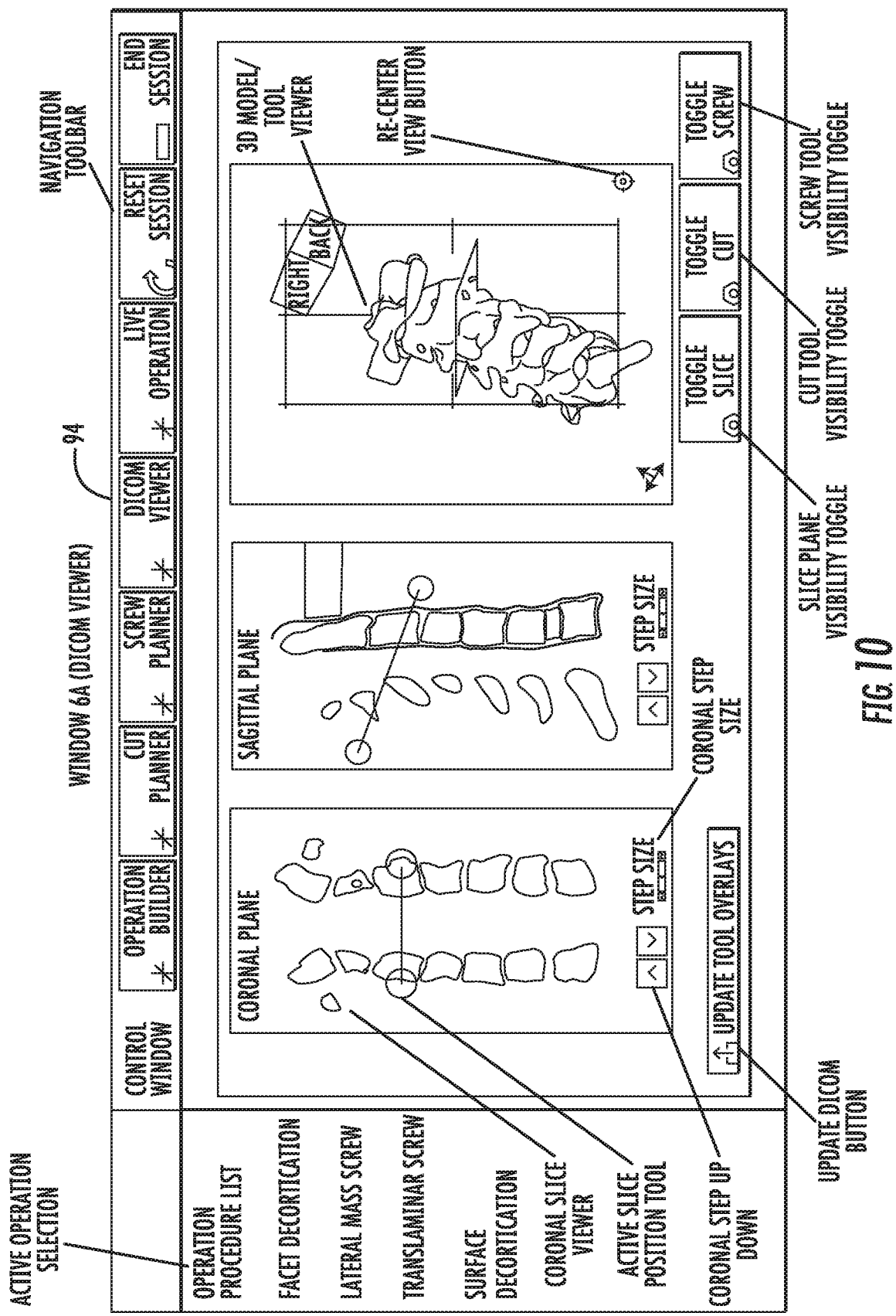
FIG. 10 is a screen shot illustrating a (DICOM) digital imaging and communications in medicine screen for the present system for viewing the patient's anatomy.
Figure 11:
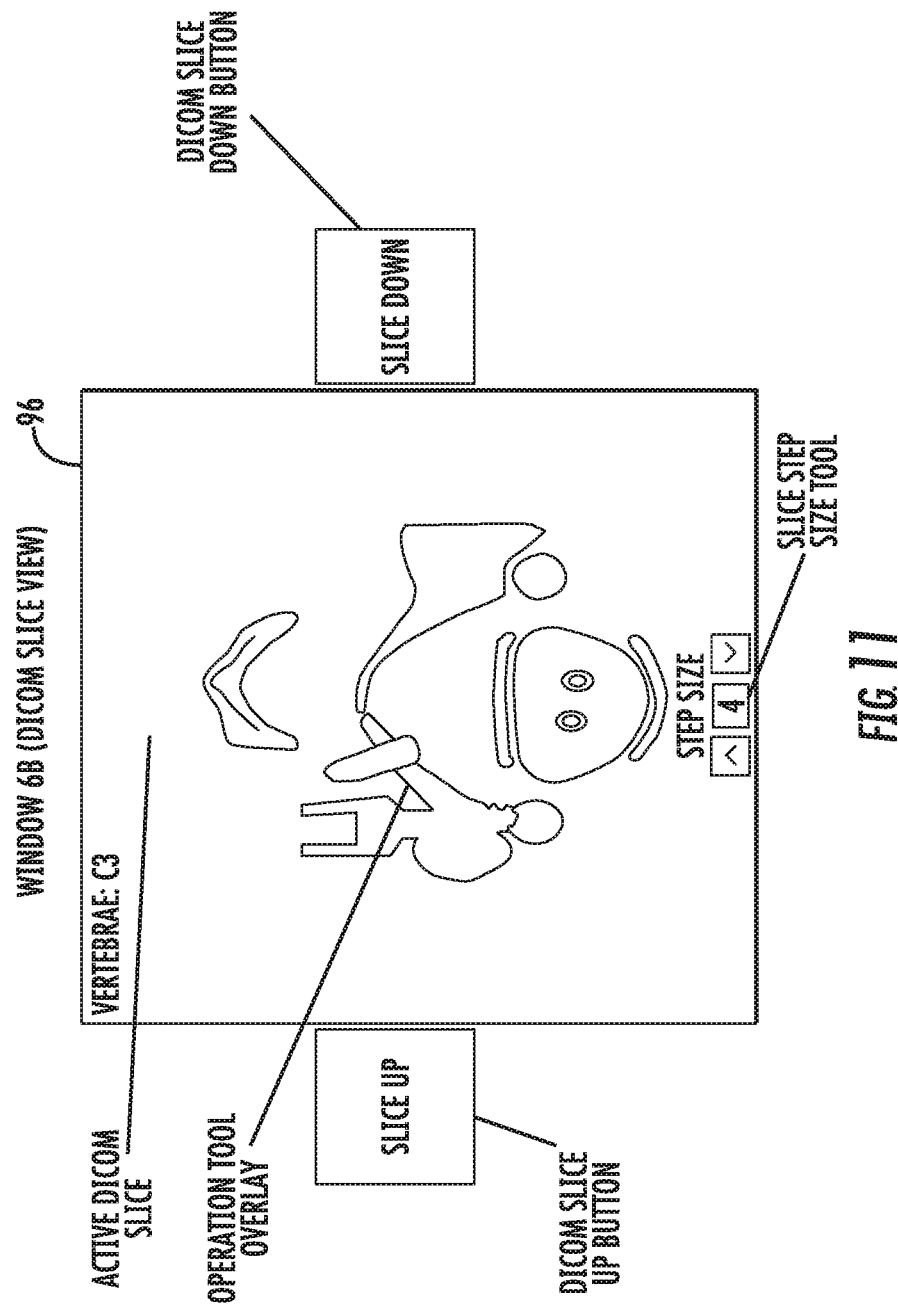
FIG. 11 is a screen shot illustrating a DICOM slice view screen for the present system.

Referring to FIGS. 8 and 9, planning the insertion of screw screens 70, 72 are illustrated. In these screens, the system 10 allows the operator 68 to edit a specific procedure as selected from the Operation Procedure List 54 (FIG. 5) on the right side of the screen. This screen allows the operator 68 to select a desired vertebrae 62 for examination, rotation and positioning, to allow an axis of insertion 76 to be oriented in the vertebrae. Each procedure can include operations on any number of vertebrae, and may include the insertion of pedicle screws 74. Pedicle screws 74 typically include a threaded shank 78 and tulip portion 80. The tulip portion 80 is typically formed to have two upright arms 82 for accepting a rod member (not shown) for connecting multiple screws together to allow fusion of the vertebrae 62 to adjacently positioned vertebrae 62. The pedicle screw 74 is connected to a tube or non-tubular member (not-shown) that immobilizes and orients the upright arms 82 of the tulip portion 80, while engaging the shank 78 so that the screw can be inserted along an axis 76 chosen by the operator 68, and to a desired depth in the vertebrae 62 with the upright arms 82 oriented to allow a rod to be inserted across multiple pedicle screws 74. The tool 92 for inserting the screw, like the other tools 92 (often referred to as an effector), includes a length and a diameter (that may change over its length) stored in the tool offsets, whereby the system knows the length and diameter of the tool for planning and insertion of the screw. This construction thereby provides warnings and notices to the operator 68 if there is interference with the chosen path, or if the screw will protrude from the bone in an undesirable manner. In one embodiment, the control system 10 utilizes the volume of the vertebrae to predict break out or collision to protect the patient from injury, and may also track nerve space, other vertebrae, other tools and sensitive tissue areas of the patient to avoid injury. It should also be noted that, while pedicle screws are illustrated herein, any type of bone screw may be inserted in a similar manner without departing from the scope of the invention.

Figure 12:
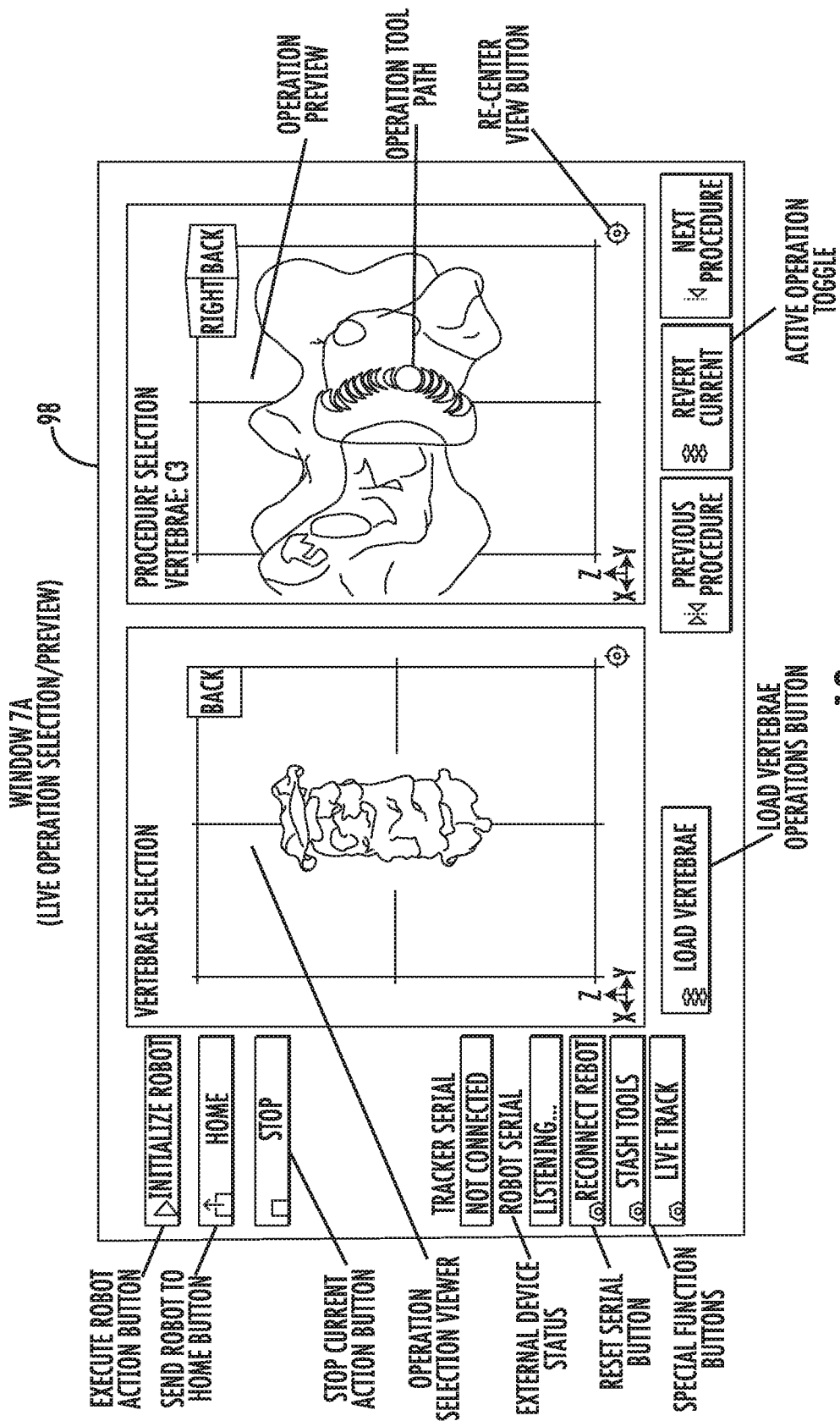
FIG. 12 is a screen shot illustrating an operation preview screen for the present system.
Figure 13:
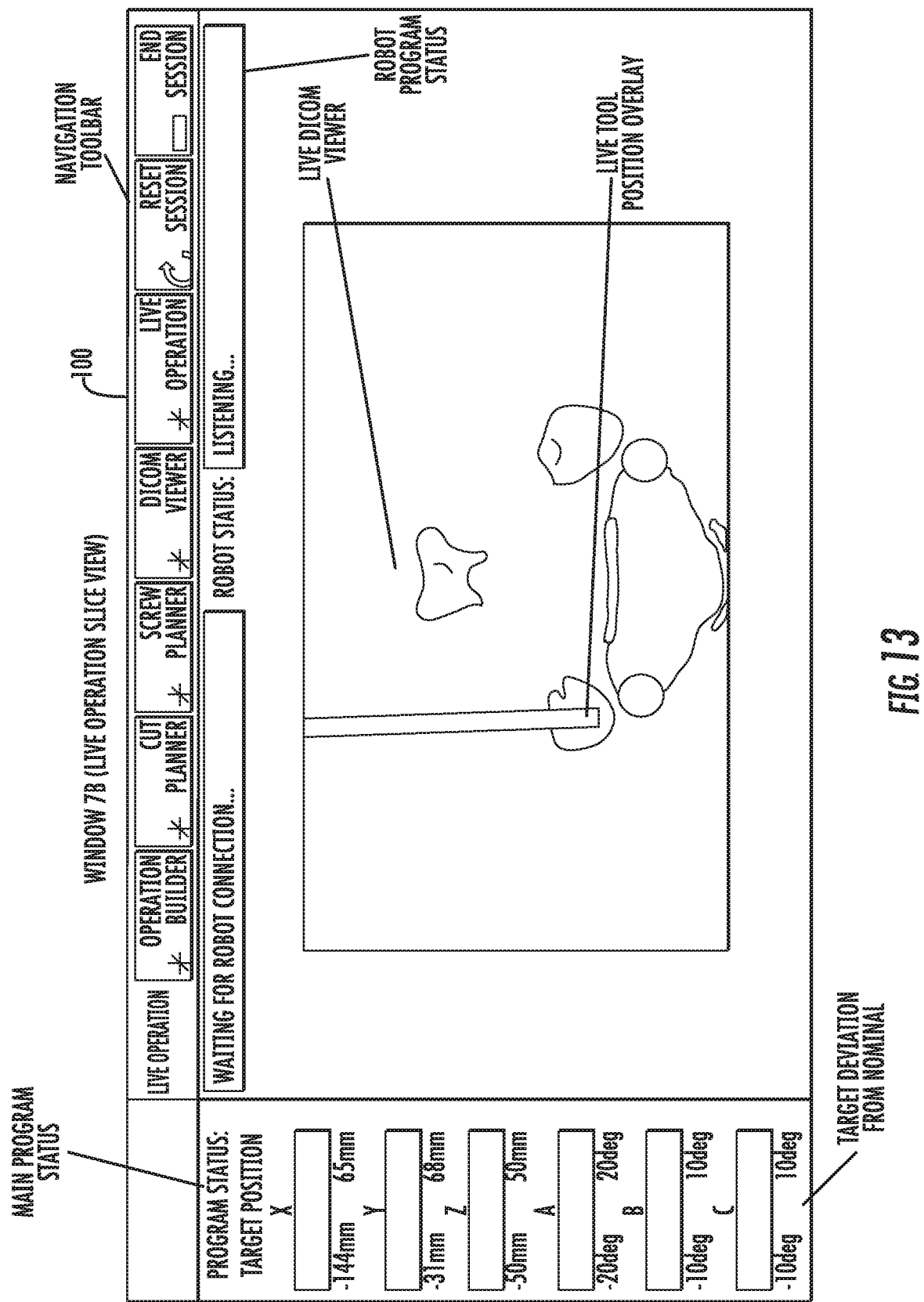
FIG. 13 is a screen shot illustrating an operation preview screen in slice format for the present system.
Figure 14:
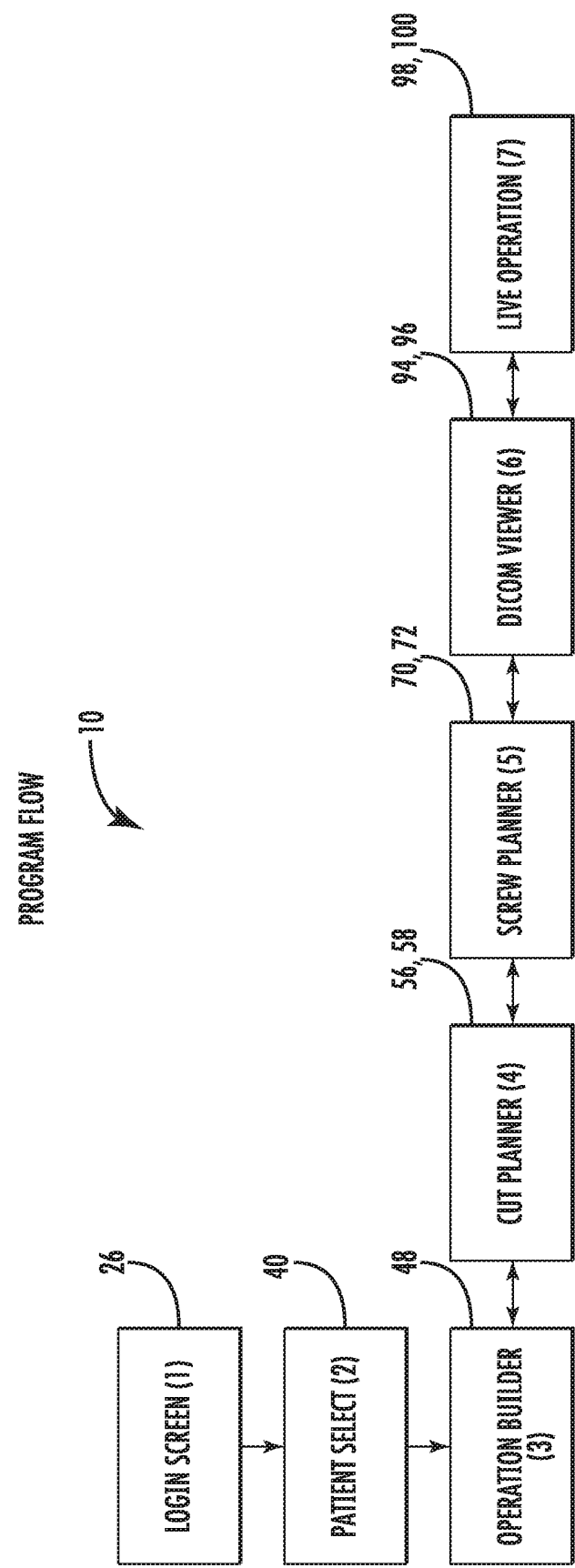
FIG. 14 is a general flow diagram for the present system.
Figure 15:
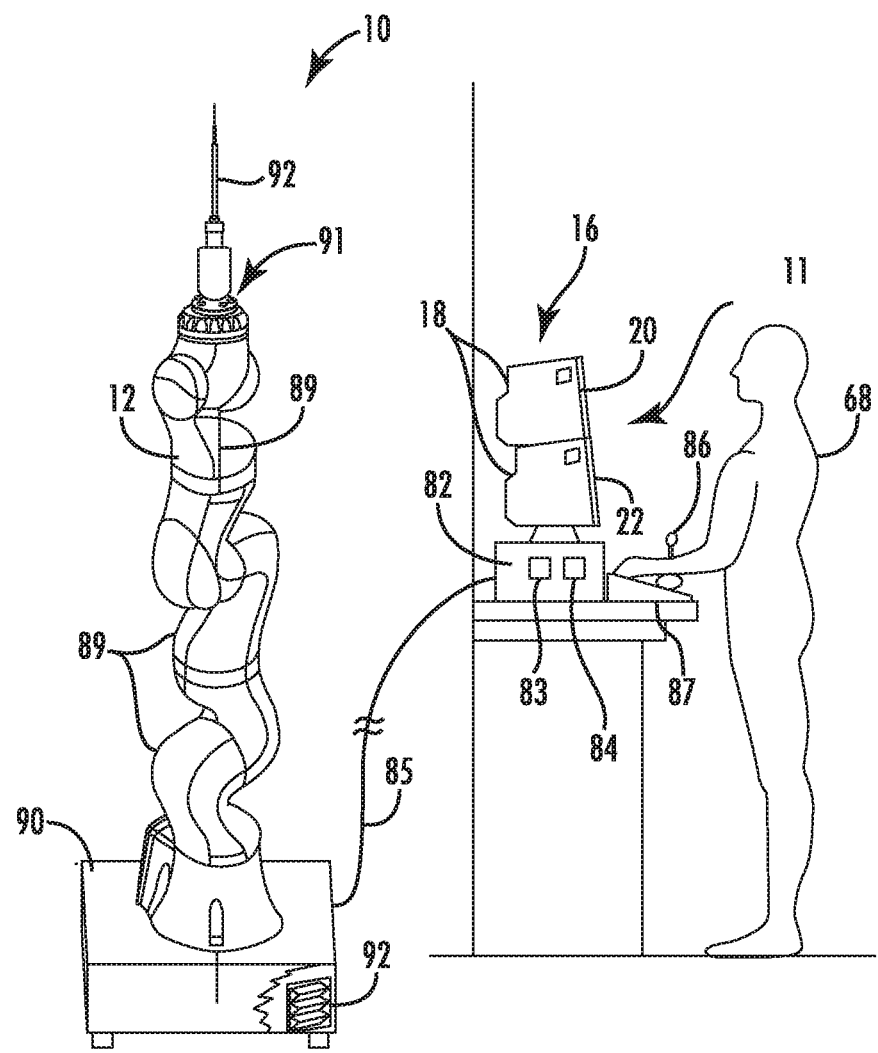
FIG. 15 is a view of the robotic control system including one embodiment of the robot.

Referring to FIGS. 10-14, the digital imaging and communications in medicine "DICOM" viewer screens 94, 96, as well as the operation overview screens 98, 100, are illustrated. In these screens, patient 3D simulated imaging in the DICOM format is loaded into the control system 10 to facilitate angled slice viewing. A 3D simulated image is often simply referred to as a 3D image, even though it is displayed on a two dimensional screen. Tools 92 and surgical tool paths 60 for each selected tool can be overlaid upon the DICOM data to show precisely where the tools will enter and traverse according to the tool paths and tools that have been selected and set up for the operation (FIGS. 12 and 13). Electromagnetic or optical sensors may be utilized to align the DICOM data with the tool paths for robot operation. In this manner, the operator 68 can see precisely where cuts will be made and the depth to which the tools will travel in the anatomy of the patient. This allows preliminary run through of the surgery to allow for modification if desired. In at least one embodiment, the control system 10 provides automatic segmentation and calibration of the DICOM data. In this embodiment, the control system 10 will automatically correlate previously taken DICOM data to the current patient on the table to facilitate live surgical tool path generation and tracking. Either anchor positions or ultrasound sweeping, or a combination of both, will allow the robot 12 to build up precision, relating the DICOM data to the real time patient data until a sufficient match is achieved to begin the operation. This construction also allows minimally invasive surgery "pathing"; whereby the control system includes path generation and planning software that provides for a minimally invasive mode. This mode will optimize robot tool trajectories so that the smallest possible incision (ideally just a single puncture) can be used. Both surface and/or internal tissue damage can be minimized or preferentially protected as per the operator's discretion.

What is claimed is:

1. A robotic surgical system comprising:
   a multi-axis surgical robot with a plurality of movable components and operable to hold and operate a surgical tool;
   a computer system having a processor, a display device and an input device, the computer system connected to the robot for controlling operation of the surgical tool and movement of the robot components to move the surgical tool, the computer system being configured to receive one or more images of a surgical site and display on the display device at least one of the images upon command received through the input device, the display device being operable to receive information from a user about a proposed surgical tool path overlaid on the at least one image for the surgical tool, the processor directing movement of the surgical tool to perform a surgical procedure at the surgical site based on processing of the proposed path instruction;
   the computer system further configured to determine the location of the surgical tool relative to the surgical site prior to surgical operation based on a predetermined surgical tool offset including an offset length and diameter of the surgical tool.

2. The system of claim 1, wherein the computer system is configured to receive a tool type among a plurality of surgical tools, each selected tool type having an associated tool length and diameter for use by the computer system.

3. The system of claim 1, wherein the surgical tool is a cutting tool and the computer system is configured to determine the location of the cutting tool based on the offset length and cutting diameter of the cutting tool.

4. The system of claim 1, wherein the computer system generates a warning to the user if the proposed surgical tool path creates an interference with the surgical tool.

5. The system of claim 1, wherein the surgical tool is a screw insertion tool and the computer system generates a warning to the user if a screw will protrude from a bone based on the proposed surgical tool path.

6. The system of claim 1, wherein the computer system is configured to display at least one simulated 3D image of the surgical site and show a currently predicted surgical tool path and surgical tool location on the displayed image and allow the user to adjust a current predicted path to a new predicted path.

7. The system of claim 6, wherein the computer system is configured to display an operation builder screen having a plurality of selectable operation procedures for selection to at least partially program operation of the robot and the surgical tool.

8. The system of claim 1, wherein the processor determines the surgical tool path and provides surgical tool path data to the robot to effect movement of the tool along the movement path.

9. The system of claim 8, wherein the processor is configured to analyze the proposed surgical tool path and effect changes to the surgical tool path.

10. The system of claim 1, wherein the computer system is configured to display an operation builder screen having a plurality of selectable operation procedures for selection to at least partially program operation of the robot and the surgical tool.

11. A robotic surgical method comprising:
    positioning a multi-axis surgical robot with a plurality of computer system controlled movable components adjacent to a surgical patient;
    activating a computer system having a processor, a display device and an input device, the computer system connected to the robot for controlling operation of a surgical tool held by the robot and movement of the components to effect movement of the surgical tool, the computer system being configured to receive one or more images of a surgical site;
    displaying at least one of the surgical site images on the display device;
    receiving, through the input device, a user input of a proposed surgical path;

overlaying a proposed surgical path for the surgical tool on the displayed surgical site image based on the user input;

processing information about the proposed surgical path and the surgical tool and sending instruction to the robot to move the surgical tool along the proposed surgical path and performing a surgical procedure based on an offset length and diameter of the surgical tool, the proposed surgical path instruction being processed by the processor and used to direct movement of the tool to perform a surgical procedure at the surgical site.

12. The method of claim 11, further comprising receiving by the computer system selection of a tool type among a plurality of surgical tools, each selected tool type having an associated tool length and diameter for use by the computer system.

13. The method of claim 11, wherein the surgical tool is a cutting tool and the computer system is configured to determine the location of the cutting tool based on the offset length and cutting diameter of the cutting tool.

14. The method of claim 11, further comprising generating a warning to the user if the proposed surgical tool path creates an interference with the surgical tool.

15. The method of claim 11, wherein the surgical tool is a screw insertion tool, the method further comprising generating a warning to the user if a screw will protrude from a bone based on the proposed surgical tool path.

16. The method of claim 11, wherein the computer system is configured to display at least one simulated 3D image of the surgical site and show a currently predicted surgical tool path and surgical tool location on the displayed image and allow the user to adjust a current predicted path to a new predicted path.

17. The method of claim 16, wherein the computer system is configured to display an operation builder screen having a plurality of selectable operation procedures for selection to at least partially program operation of the robot and the surgical tool.

18. The method of claim 11, wherein the processor determines the surgical tool path and provides surgical tool path data to the robot to effect movement of the tool along the movement path.

19. The method of claim 18, wherein the processor is configured to analyze the proposed surgical tool path and effect changes to the surgical tool path.

20. The method of claim 11, wherein the computer system is configured to display an operation builder screen having a plurality of selectable operation procedures for selection to at least partially program operation of the robot and the surgical tool.

* * * * *